DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MARCH 10, 1970

872 O.G. 357

T872,001

5-TERTIARY BUTYL-1,3-CYCLOHEXANEBIS-(METHYLAMINE)

Marvin A. McCall and John R. Caldwell, both of P.O. Box 511, Kingsport, Tenn. 37662

Filed Jan. 15, 1968, Ser. No. 697,582

Int. Cl. C07c *87/38;* C08g *17/00, 17/02*

U.S. Cl. 260—563

No Drawing. 8 Pages Specification

5-tertiary butyl-1,3-cyclohexanebis(methylamine) having the structural formula:

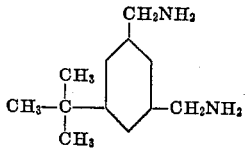

is useful in the preparation of linear, condensation polymers having improved glass transition temperatures.